(12) United States Patent
He et al.

(10) Patent No.: US 9,006,482 B2
(45) Date of Patent: Apr. 14, 2015

(54) PROCESS FOR PREPARING METHYLENE BIS-(DIALKYLAMINO-DITHIOFORMATE) IN ONE STEP

(71) Applicants: China Petroleum & Chemical Corporation, Beijing (CN); Research Institute of Nanjing Chemical Industrial Group, Nanjing (CN)

(72) Inventors: Zhiyong He, Nanjing (CN); Wei Huang, Nanjing (CN); Weiwei Kong, Nanjing (CN); Lei Ren, Nanjing (CN); Junyan Ping, Nanjing (CN)

(73) Assignees: China Petroleum & Chemical Corporation, Beijing (CN); Research Institute of Nanjing Chemical Industrial Corporation, Nanjing (CN)

( * ) Notice: Subject to any disclaimer, the term of this patent is extended or adjusted under 35 U.S.C. 154(b) by 0 days.

(21) Appl. No.: 14/307,849

(22) Filed: Jun. 18, 2014

(65) Prior Publication Data

US 2014/0371483 A1    Dec. 18, 2014

(30) Foreign Application Priority Data

Jun. 18, 2013    (CN) .......................... 2013 1 0240899

(51) Int. Cl.
*C07C 313/00*    (2006.01)
*C07C 333/20*    (2006.01)

(52) U.S. Cl.
CPC .................................. *C07C 333/20* (2013.01)

(58) Field of Classification Search
None
See application file for complete search history.

(56) References Cited

U.S. PATENT DOCUMENTS

| | | |
|---|---|---|
| 3,816,550 A | 6/1974 | Young et al. |
| 3,876,550 A | 4/1975 | Holubec |
| 5,015,368 A | 5/1991 | Di Biase et al. |
| 5,744,629 A | 4/1998 | Jover et al. |

FOREIGN PATENT DOCUMENTS

| | | | |
|---|---|---|---|
| CN | 1364759 | * | 8/2002 |
| CN | 1159294 C | | 7/2004 |

* cited by examiner

*Primary Examiner* — Karl J Puttlitz
(74) *Attorney, Agent, or Firm* — Buchanan Ingersoll & Rooney PC

(57) ABSTRACT

A process for preparing methylene bis-(dialkylamino-dithioformate) in one step includes: simultaneously feeding all or part of four raw materials: dialkylamine, an aqueous solution of sodium hydroxide, dichloromethane and carbon disulfide through a constant-flow pump into a continuous flow reactor; performing the reactions in the continuous flow reactor under a temperature of 10 to 100° C. and with a residence time of 10 to 100 s; simply separating of the obtained reaction products to give the final product. The process synthesizes the product in one step by using the continuous flow reactor. The rapid mass transfer and heat transfer in the continuous flow reactor promote the main reaction, reduce side reactions, improve the product color, and shorten the operation time. Moreover, the yield is relatively high and the quality of the final product meets the requirements.

18 Claims, 1 Drawing Sheet

PROCESS FOR PREPARING METHYLENE BIS-(DIALKYLAMINO-DITHIOFORMATE) IN ONE STEP

TECHNICAL FIELD OF THE INVENTION

The invention belongs to the field of the organic synthesis of methylene bis-(dialkylamino-dithioformate).

BACKGROUND ART

As is well-known, oil products are inevitably in contact with oxygen in the air and metallic surfaces during use and undergo oxidizing reactions, thus becoming deteriorated. As a result, the viscosity and acid number of oil products are increased, oil sludge and sediment are produced and corrosion and abrasion of metal parts are caused. Adding antioxidants to oil products can effectively suppress the oxidation of oil products, increase the useful life and improve the service performance thereof.

When used in oil products, methylene bis-(dialkylamino-dithioformate) exhibits notable anti-oxidation, good abrasion resistance and extreme pressure performances, and meanwhile, the characteristics of good oil solubility, being ash free and others. It is widely used in many types of oil products, such as steam-turbine oil, hydraulic oil, gear oil, internal combustion engine oil, and lubricating greases.

The conventional preparation process of methylene bis-(dialkylamino-dithioformate) is carried out in two steps: the first step is to react dialkylamine with carbon disulfide in the presence of an alkaline solution of sodium hydroxide, and the second step is to further subject the product of the aforesaid reaction to alkylation reaction by using dichloromethane. Because the reaction of the first step is strong exothermic, the addition of the raw materials must be properly controlled to prevent the local temperature from rising so rapidly that side reactions are increased, which affects the product quality.

Several patents have described carrying out the aforesaid synthesis for the preparation of methylene bis-(dialkylamino-dithioformate) on a production scale of 0.5 to 2.0 kg. U.S. Pat. No. 3,876,550 uses a two-step process to prepare methylene bis-(dialkylamino-dithioformate). Considering that an overly high viscosity of the materials during the reaction at low temperature makes the mixing non-homogeneous and further affects the reaction, toluene and isopropanol are added as the solvents for dilution so as to reduce the viscosity of the reaction system. However, the actual yield of only about 40% is not high, and there is an additional operation of recovering solvents. Besides, the residual solvent in the obtained product would affect the product quality.

U.S. Pat. No. 5,015,368 uses a process to prepare methylene bis-(dialkylamino-dithioformate) in two steps. According to the process, the viscosity of the reaction system is reduced by increasing the reaction temperature instead of adding diluents. The color of the product produced by this process is comparatively dark and the yield is not high.

U.S. Pat. No. 5,744,629 discloses a process for preparing methylene bis-(dialkylamino-dithioformate) with a lighter color. The main purpose of this process is to improve the product color. By adding $CS_2$ dropwise at a low temperature during the reaction and subsequently performing vacuum distillation of the resultant organic phase twice, the colourity of the product is reduce and the yield is increased. However, the operations of this process are rather complicated.

Chinese patent CN1159294 discloses a reaction process comprising adding ethanol as a solvent, mixing dichloromethane, dialkylamine and an aqueous solution of NaOH at the same time, and then adding $CS_2$ dropwise. The main purpose of this process is to shorten the reaction time and prepare a qualified product. However, this process is also a two-step process.

In the traditional techniques, a two-step synthesis process is used for preparing methylene bis-(dialkylamino-dithioformate). All of the reactions occur in several reaction glass bottles or reaction kettles, and reactions are carried out intermittently. In the first step, carbon disulfide and alkylamine react in the aqueous solution of sodium hydroxide to yield a sodium salt of dialkyldithiocarbamic acid. Because the reaction releases a great amount of heat, $CS_2$ is added dropwise; furthermore, the dropping time is comparatively long, and a relatively low temperature should be maintained for the reaction. The reaction equation is as follows:

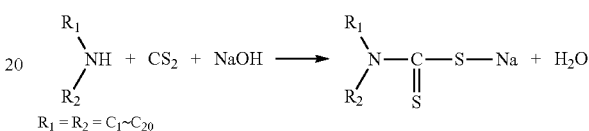

In the second step, the sodium salt prepared above is alkylated with methylene dichloride to obtain the target product. The reaction equation is as follows:

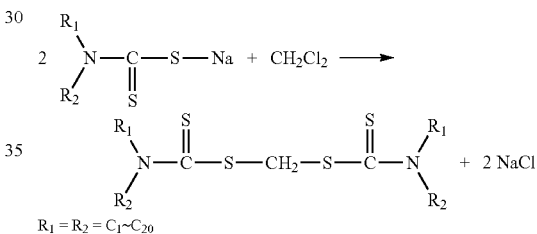

According to U.S. pat. No 3,876,550, 627 g of di-n-butylamine, 240 g of a 50% aqueous solution of sodium hydroxide, 200 g of toluene, and 200 g of isopropanol are mixed; then 228 g of carbon disulfide is slowly added to the above mixture over a period of 5 hours, and the temperature of the mixture is maintained at or under 42° C. After completion of the reaction, the mixture is slowly heated to not higher than 65° C. to expel unreacted carbon disulfide. Then 225 g of methylene dichloride is added slowly to the reaction mixture over a period of 2.5 hours, meanwhile the temperature is increased to 75° C. After the addition of the methylene dichloride, the temperature of the mixture is maintained at a temperature of 60 to 65° C. for an additional 2.5 hours. The mixture is then washed with a 150 ml of water three times; the volatile components are removed from the reaction mixture through vacuum distillation at a pressure of 120 mm Hg and a temperature of 122° C. The precipitated sodium chloride is separated from the product by a filtration method.

U.S. Pat. No. 5,015,368 discloses a process for preparing methylene bis-(dialkylamino-dithioformate) in two steps. In the first step, carbon disulfide is added to a mixture of di-n-butylamine and an aqueous solution of sodium hydroxide at a temperature of about 63° C.; in the second step, the reaction mixture is heated to 88° C., and methylene dichloride is added to the aforesaid reaction mixture over four hours. After the addition of methylene dichloride, the mixture is reacted for an additional three hours at a temperature in the range of 85° C.

to 88° C. After the reaction is completed, the liquid phase is separated, and subjected to vacuum distillation to yield the product. The product has a kinematic viscosity of 15.5 cSt, a nitrogen content of 6.8 and a ASTM colour of 1.0.

U.S. Pat. No. 5,744,629 discloses a process for preparing methylene bis-(dialkylamino-dithioformate) with a lighter color. First, the solution of sodium hydroxide and di-n-butylamine reacts with carbon disulfide in an autoclave with the temperature being kept at or below 15° C. over a reaction time of 0.5 hour. An excess amount of methylene dichloride is slowly added dropwise with the temperature gradually increased. The reaction takes place at a temperature of 75° C. to 80° C. for 2 hours. After the reaction is completed, a distillation under reduced pressure of the obtained products is performed in two steps: in the first step, the vacuum distillation is conducted at a temperature between 45° C. and 100° C. and at a pressure of 5 to 50 kPa, then phase separation is carried out at a temperature between 35° C. and 50° C.; in the second step, the separated organic phase is subject to a distillation under reduced pressure under the same conditions as those of the first step. The product with ASTM colour of less than 2 can be finally obtained.

CN 1159294 discloses the preparation of methylene bis-(dialkylamino-dithioformate). Carbon disulfide is added to a mixture comprising dialkylamine, an aqueous solution of sodium hydroxide, dichloromethane and ethanol as a solvent at 10 to 60° C., and the mixture is reacted for 0.5 to 5 hours. Then the temperature is increased to 50° C. to 100° C., the reaction of the mixture continues for 1 to 12 hours. The product is obtained by separation.

It can be seen from the above introduction that in the prior art, usually first, carbon disulfide is added dropwise into the mixture of the aqueous solution of sodium hydroxide and dialkylamine and reacts the ensemble for a period of time, and then dichloromethane is added dropwise for continuing the reaction, wherein the dropping times of carbon disulfide and of dichloromethane are relatively long, so is the reaction time needed. Meanwhile, these methods are performed intermittently, and the operations of the reactions are complicate.

The aforesaid reactions are all performed in the conventional reaction kettles or glass bottles in batch mode, which has many disadvantages, such as long reaction time, huge amount of reaction heat, difficult temperature control, high viscosity of materials, non-homogeneous mixing, a large number of side reactions and by-products, poor colors of products etc. Improvements can be made by increasing the stirring speed, adding diluting solvents or increasing the flow rate of conveying cooling fluid. However, the rapid and homogeneous mixing of materials within a short time and the fast removal of reaction heat cannot be realized. Thus, the effects of these improvements are limited.

SUMMARY OF THE INVENTION

The main object of the invention is to provide a process for preparing methylene bis-(dialkylamino-dithioformate) which can overcome the shortcomings of the processes in the prior arts. The inventors surprisingly find that by simultaneously supplying the raw materials: dialkylamine, carbon disulfide, an aqueous solution of sodium hydroxide and dichloromethane through a fluid conveying equipment into a reaction system of the continuous flow tubular reactor type, methylene bis-(dialkylamino-dithioformate) can be prepared by a one-step reaction. More specifically, the inventors unexpectedly find that by simultaneously supplying reaction materials through a constant-flow pump into the continuous flow tubular reactor having a channel diameter of about 0.1 μm to 3 mm and meanwhile, connecting the reactor with the high-low-temperature circulation tank system to control the temperature of the reactor, the reactants can be fully mixed when flowing within a short period, the huge amount of reaction heat released instantaneously during the reaction can be removed timely, the reaction temperature can be maintained within a quite small fluctuation range, the reaction time is significantly shortened, the number of side reactions is reduced, the reaction yield is increased and product quality is improved. Meanwhile, higher production efficiency and modest reaction pressure can be achieved. In other words, the process of the invention can result in a good compromise among the aspects of reaction rate, reaction yield, quality of reaction products and reaction control.

Thus, one subject of the invention is a process for preparing methylene bis-(dialkylamino-dithioformate) in one step, characterized in that the process uses dialkylamine, sodium hydroxide, carbon disulfide and dichloromethane as raw materials and comprises simultaneously supplying the raw materials into a continuous flow tubular reactor with a channel diameter of about 0.1 μm to 3 mm, and reacting the raw materials in one step under the reaction temperature maintained at about 10 to 100□.

Wherein said methylene bis-(dialkylamino-dithioformate) is, more particularly, a compound of formula (I):

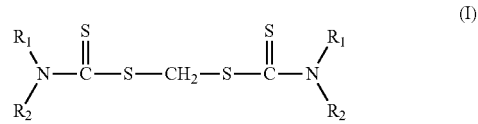

wherein $R_1$ and $R_2$, identical or different, are independently a $C_1$ to $C_{20}$ alkyl, preferably n-butyl, ethyl, propyl, n-amyl.

This process for preparing methylene bis-(dialkylamino-dithioformate) can reduce the two reaction steps in the existing process to one reaction step, thus extraordinarily can save reaction and operation time. Moreover, compared to the existing processes in the prior arts, the process of the invention can reduce side reactions, so impurities in products are decreased, product yield is increased and a good product color is obtained.

The process for synthesizing methylene bis-(dialkylamino-dithioformate) of formula (I) in one step as proposed in the invention involves the following reaction equation:

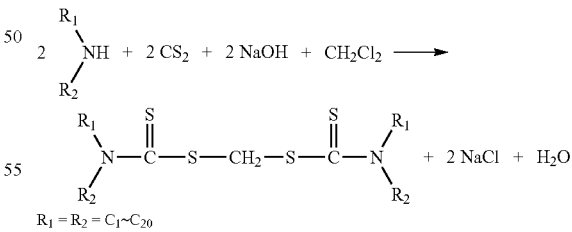

wherein $R_1$ and $R_2$, identical or different, are independently a $C_1$ to $C_{20}$ alkyl, preferably n-butyl, ethyl, propyl, n-amyl.

According to one embodiment of the process of the invention, all or part of the four raw materials, namely, dialkylamine, carbon disulfide, dichloromethane and an aqueous solution of sodium hydroxide, are simultaneously fed through a constant-flow pump into a continuous flow tubular reactor with a channel diameter of about 0.1 μm to 3 mm, the reaction is performed in one step under the temperature controlled at about 10 to 100° C. and the pressure controlled at about 100 to 1800 kPa, and the residence time of the reaction is controlled to be about between 10 s and 100 s; after the completion of the reaction, the obtained products are subjected to a phase separation, an atmospheric and/or vacuum distillation and a filtration to remove sodium chloride, and finally give a methylene bis-(dialkylamino-dithioformate) compound in a transparent liquid form.

The channel diameter of the continuous flow tubular reactor used in the process of the invention is generally the order of millimeter or micron, generally about 0.1 µm to 3 mm, and preferably about 10 µm to 1000 µm, and more preferably about 20 µm to 200 µm.

The continuous flow tubular reactor used in the process of the invention can be made of stainless steel, glass, ceramic, poly(tetrafluoroethylene), inorganic silicon or Peek materials.

According to one embodiment of the process of the invention, the continuous flow tubular reactor used in the invention includes one reaction plate or a plurality of reaction plates connected in series through which the reactants can continuously flow, preferably it includes 2 to 8 reaction plates. Said reaction plate consists of two heat transfer layers and one layer for carrying out reaction (hereafter it is known as "reaction layer"), the middle layer being the reaction layer. The reaction spaces in said reaction layer are the spaces in the shape of heart or similar to heart formed by channels, each of the heart-shaped spaces formed by channels being connected in series by the channels having a diameter of about 0.1 µm to 3 mm, preferably about 10 µm to 1000 µm, and more preferably about 20 µm to 200 µm. The temperature required for the reaction is attained by controlling the reactor temperature through a heat conducting fluid, which heat conducting fluid is selected from one of water, saturated steam, mineral oil or diphenyl mixture.

According to one embodiment of the process of the invention, the reaction temperature of said process is generally controlled at about 10 to 100° C., preferably about 40 to 90° C., and more preferably about 50 to 80° C.

According to one embodiment of the process of the invention, the reaction pressure of said process is controlled at about 100 to 1800 kPa, preferably about 200 to 1600 kPa, further preferably about 300 to 1200 kPa, and more preferably about 300 to 1000 kPa.

According to one embodiment of the process of the invention, the residence time of said process is controlled to be about 10 to 100 s, preferably about 24 to 96 s.

In the studies, the inventors find that when a continuous flow tubular reactor with a channel diameter greater than 3 mm is used to carry out the reaction, the quality and the yield of the product are both greatly influenced: the yield is reduced and the ASTM colour of the product is rather bad. This phenomenon is closely related to the heat transfer efficiency of the reactor, and thus the channel diameter. With the same volume, the reactor having a smaller channel diameter possesses a greater internal specific area than the reactor having a greater channel diameter, and thus the heat transfer efficiency of the former is better than that of the latter. Once the reaction heat can not be removed timely, it will cause the occurrences of side reactions and affect the quality of the obtained product. However, an overly small channel diameter affects production efficiency and results in an unduly high operation pressure, and thus increases the production costs. Not wishing to be related to a particular theory, the applicant unexpectedly finds that within the scope of the invention, if the temperature difference, the residence time and the channel diameter of the continuous flow tubular reactor conform to the following relation formula (wherein $\Delta T<2$, in K), the process of the invention can achieve the optimum technical effect:

$$\Delta T = k \times \frac{d}{4tU}$$

in the above formula:

$\Delta T$ represents the numerical value of the temperature difference between the inside and the outside of the reaction plate measured in K;

U represents the numerical value of the heat transfer coefficient of the reaction plate measured in $W/\mu m^2 \cdot K$, it depends on the materials used;

d represents the numerical value of the channel diameter of the reactor measured in µm;

t represents the numerical value of the residence time measured in s;

k represents an empirical coefficient, wherein $1.87 \times 10^{-9} \leq k \leq 3.74 \times 10^{-10}$.

When $\Delta T$, which is the temperature difference between the inside and the outside of the reaction plate, is smaller than 2K, it is deemed that the reaction heat can be removed timely, and the system temperature can be considered as the reaction temperature.

According to one embodiment of the process of the invention, the continuous flow tubular reactor used in the invention is made of for example, but not limited to, glass with the heat transfer coefficient U of $1.7 \times 10^{-9}$ $W/\mu m^2 \cdot K$. Under normal reaction circumstances, the residence time is controlled to be between 10 and 100 s, and the channel diameter is optimally selected to be 20 to 200 µm, wherein the value of k is related to the reaction type and comes in the range of $1.87 \times 10^{-9}$ to $3.74 \times 10^{-10}$, including the end values.

From the aforesaid relation formula, it can be seen that the smaller the channel diameter of the continuous flow tubular reactor is, the smaller $\Delta T$ is (which means heat has been timely removed), and the better the effects of mass transfer and heat transfer are; however if the channel diameter of the continuous flow tubular reactor is smaller, the mass transfer resistance will be increased, the residence time will be increased, and the production efficiency will be reduced. Therefore, it is not true that the smaller the channel diameter is, the better the technical effect is. When the channel diameter is chosen to be 20 to 200 µm, for example according to Example 1 given below, $\Delta T$ calculated from this formula is 0.1 K. When the channel diameter of the continuous flow tubular reactor is overly big (exceeding 3000 µm), the temperature difference $\Delta T$ is increased. This means that the heat produced during the reaction is not timely removed, and there is the risk of losing control of the reaction temperature. Since the value of $\Delta T$ calculated in Comparative Example 9 given below is 3.5 K, which exceeds the aforesaid value as specified, the reaction yield and the quality of the reaction product obtained in Comparative Example 9 are greatly influenced.

The process of the invention is generally performed as follows: first, the temperature of the continuous flow tubular reactor is set at about 10 to 100° C., preferable about 40 to 90° C., and more preferably about 50 to 80° C., and the pressure is set at about 0.1 to 1.8 Mpa, preferably about 0.2 to 1.6 Mpa, preferably about 0.3 to 1.2 Mpa, and more preferably about 0.3 to 1.0 Mpa; then the four raw materials: an aqueous solution of sodium hydroxide, dialkylamine, dichloromethane and carbon disulfide, are simultaneously supplied into the reactor through a constant-flow pump and reacted herein, wherein the residence time is about 10 to 100 s, preferably about 24 to 96 s; after the completion of the reaction, the oil-water phase separation of the obtained products is performed, and water is added to wash the organic phase, then the organic phase is separated; afterwards, the unreacted raw materials, by-products and a small amount of water are removed by means of atmospheric and/or vacuum distillation; then through filtration, a yellow product in a transparent liquid state is obtained.

Said dialkylamine is the one having alkyl containing 1 to 20 carbon atoms, preferably di-n-butylamine. As dialkylamine has a relatively high boiling point, it is not easy to remove it from the product, thereby affecting the product quality. Therefore, the ratios of the other raw materials should be properly increased to more completely consume dialkylamine. Generally, the molar ratio of dialkylamine to carbon disulfide is chosen to be about 1:1 to 1:1.7, and preferably about 1:1 to 1:1.4. The molar ratio of dialkylamine to sodium hydroxide is chosen to be about 1:1 to 1:1.6, preferably about 1:1 to 1:1.3. The molar ratio of dialkylamine to dichloromethane is chosen to be about 1:0.5 to 1:0.9, preferably about 1:0.5 to 1:0.8. The mass concentration of the aqueous solution of sodium hydroxide is chosen to be about 13% to 50%.

The pressure of said vacuum distillation method is chosen to be 5 Kpa, and the distillation temperature is about 40 to 100° C.

According to the preparation process of the invention, the addition of all the raw materials is performed simultaneously, so the time for adding materials is saved significantly. Meanwhile, this process can be conducted continuously. The heat transfer and the mass transfer of the reaction are rapid, and the charges are rapidly and homogeneously mixed. It is easy to instantly remove the heat generated during the reaction, and the reaction temperature can be precisely controlled. The reaction can rapidly advance in the direction of obtaining the product, therefore, the time of the reaction and time of the operation are greatly increased. Moreover, the side products of the reaction are reduced, the color of the product is good, the yield of the reaction is high, and the product quality meets the requirements.

SPECIAL FEEDING MODE FOR CONDUCTING THE INVENTION

Figure 1:
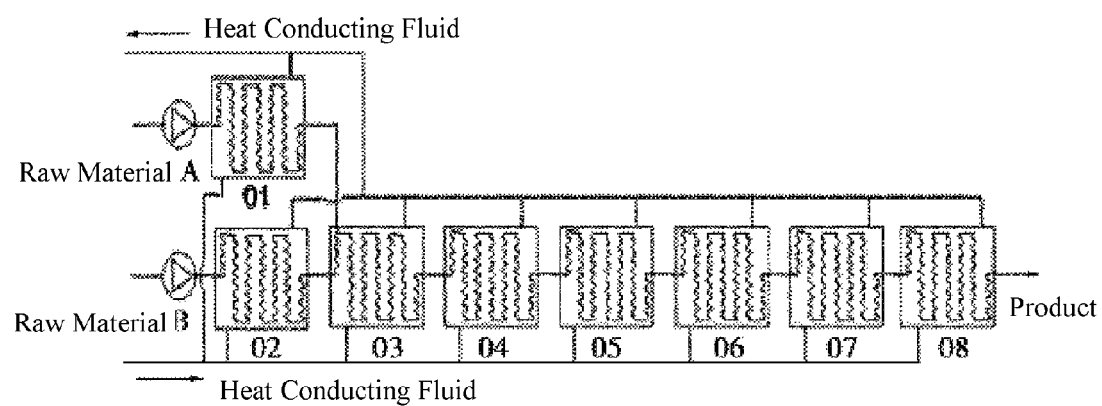
FIG. 1 is a schema illustrating the reaction procedure of the continuous flow tubular reactor in the process according to the invention.
Figure 2:
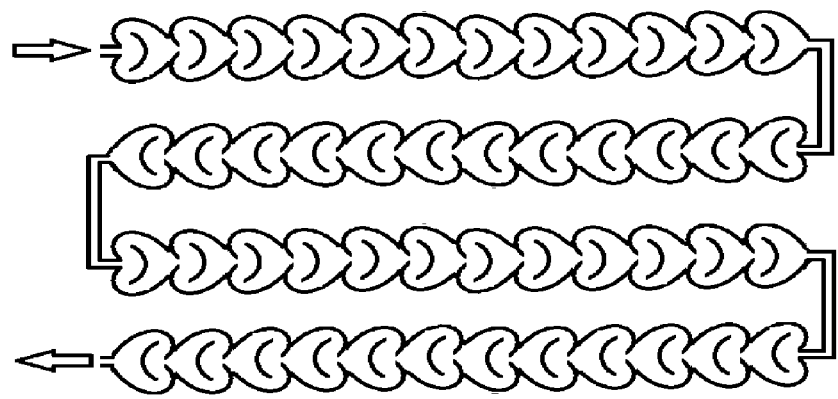
FIG. 2 is a schema illustrating the channel structure of the reaction layer in the single reaction plate.

The process of the invention may include the following several feeding modes. In light of the figures, the detailed descriptions are as follows.

Feeding mode I: raw material A is a mixture of dialkylamine and an aqueous solution of sodium hydroxide, which is fed through a constant-flow pump into a reaction plate 01. Raw material B is a mixture of carbon disulfide and dichloromethane, which is fed through a constant-flow pump into a reaction plate 02. Then, raw material A and raw material B simultaneously enter into a reaction plate 03 for a continuous reaction, and then the reactants enter into reaction plates 04 to 08 successively for continuing the reaction. For each of the plates, there is an envelope layer for a heat conducting oil which is directly connected to a high-low-temperature circulation pump, which can instantly remove the reaction heat.

Feeding mode II: raw material A is fed through the constant-flow pump into the reaction plate 02, and raw material B is fed through the constant-flow pump into the reaction plate 01. The remaining steps are the same as those of the aforesaid feeding mode I.

EXAMPLES

With the detailed description of the following examples, the details and advantages of the invention will be clearer. These examples are used to further illustrate the invention but do not intend to limit the protection scope of the invention. In the following examples, the kinematic viscosity of the product is measured according to the method of standard ASTM D445, and the ASTM colour of the product is measured according to the method of standard ASTM 1500.

Example 1

A heating-cooling circulator was used to heat and cool a continuous flow tubular reactor, and the temperature of the reactor was set at 60° C. After the temperature became stable, raw material A: a mixture fluid of 300 ml di-n-butylamine and 200 ml 30% aqueous solution of sodium hydroxide was fed through a constant-flow pump into the reactor, and the flow rate was kept at 50 ml/min; meanwhile, raw material B: a mixed solution of 110 ml carbon disulfide and 60 ml dichloromethane, was fed through a constant-flow pump into the continuous flow tubular reactor, and the flow rate was kept at 20 ml/min. The channel diameter of the reactor was 20 μm. Said raw materials were reacted in the continuous flow tubular reactor with a residence time of 55 s and under a reaction pressure of 900 kPa. After the phase separation of the resultant reaction mixture, the organic phase was washed with water, and subjected to vacuum distillation (5 kPa, 70° C.) and filtration, to give a light yellow and transparent liquid; wherein the yield was 88%. The analysis of Nuclear Magnetic Resonance (NMR) and Mass Spectrum (MS) proved that the obtained product was methylene bis-(di-n-butylaminodithioformate). The product has a kinematic viscosity of 15.2 cSt, a nitrogen content of 6.8 and the ASTM colour of the product is 1.0.

Example 2

A heating-cooling circulator was used to heat and cool a continuous flow tubular reactor, and the temperature of the continuous flow tubular reactor was set at 70° C. After the temperature became stable, raw material A: a mixture fluid of 300 ml di-n-butylamine and 200 ml 30% aqueous solution of sodium hydroxide was fed through a constant-flow pump into the continuous flow tubular reactor, and the flow rate was kept at 50 ml/min; meanwhile, raw material B: a mixed solution of 110 ml carbon disulfide and 60 ml dichloromethane was fed through a constant-flow pump into the continuous flow tubular reactor, and the flow rate was kept at 20 ml/min. The channel diameter of the reactor was 50 μm. Said raw materials were reacted in the continuous flow tubular reactor with a residence time of 55 s and under a reaction pressure of 800 kPa. After the phase separation of the obtained reaction mixture, the organic phase was washed with water, and subjected to vacuum distillation (5 kPa, 75° C.) and filtration, to give a light yellow and transparent liquid; wherein the yield was 94%. The obtained product has a kinematic viscosity of 15.3 cSt, a nitrogen content of 6.7 and the ASTM colour of the product is 1.0.

Example 3

A heating-cooling circulator was used to heat and cool a continuous flow tubular reactor, and the temperature of the continuous flow tubular reactor was set at 60° C. After the temperature became stable, raw material A: a mixture fluid of 300 ml di-n-butylamine and 150 ml 50% aqueous solution of sodium hydroxide was fed through a constant-flow pump into the continuous flow tubular reactor, and the flow rate was kept at 45 ml/min; meanwhile, raw material B: a mixed solution of 120 ml carbon disulfide and 65 ml dichloromethane, was also fed to the continuous flow tubular reactor, and the flow rate was kept at 20 ml/min. The channel diameter of the reactor was 100 μm. Said raw materials were reacted in the continuous flow tubular reactor with a residence time of 59 s and under a reaction pressure of 600 kPa. The obtained products were introduced into a four-neck flask with a condenser pipe and a stirrer, and reacted at 70° C. for additional 1 hour. After the phase-separation of the obtained reaction mixture, the organic phase was washed with water, and subjected to vacuum distillation (5 kPa, 75° C.) and filtration, to give a light yellow and transparent liquid; wherein the yield was 92%. The obtained product has a kinematic viscosity of 15.6 cSt, a nitrogen content of 6.6 and the ASTM colour of the product is 1.0.

Example 4

A heating-cooling circulator was used to heat and cool a continuous flow tubular reactor, and the temperature of the continuous flow tubular reactor was set at 65° C. After the temperature became stable, raw material A: a mixture fluid of 300 ml di-isobutylamine and 200 ml 30% aqueous solution of sodium hydroxide was fed through a constant-flow pump into the continuous flow tubular reactor, and the flow rate was kept at 50 ml/min; meanwhile, raw material B: a mixed solution of 115 ml carbon disulfide and 65 ml dichloromethane was fed through a constant-flow pump into the continuous flow tubular reactor, and the flow rate was kept at 18 ml/min. The channel diameter of the reactor was 150 μm. Said raw materials were reacted in the continuous flow tubular reactor with a residence time of 57 s and under a reaction pressure of 500 kPa. After the phase-separation of the obtained reaction mixture, organic phase was washed with water, and subjected to vacuum distillation (5 kPa, 80° C.) and filtration, to give a light yellow and transparent liquid; wherein the yield was 93%. The obtained product is methylene bis-(di-isobutylamino-dithioformate) and has a kinematic viscosity of 15.5 cSt, a nitrogen content of 6.8 and the ASTM colour of the product is 1.0.

Example 5

A heating-cooling circulator was used to heat and cool a continuous flow tubular reactor, and the temperature of the continuous flow tubular reactor was set at 60° C. After the temperature became stable, raw material A: a mixture fluid of 178 ml diethylamine and 200 ml 30% aqueous solution of sodium hydroxide was fed through a constant-flow pump into the continuous flow tubular reactor with a flow rate of 45 ml/min; meanwhile, raw material B: a mixed solution of 115 ml carbon disulfide and 60 ml dichloromethane was fed through a constant-flow pump into the continuous flow tubular reactor with a flow rate of 20 ml/min. The channel diameter of the reactor was 200 μm. Said raw materials were reacted in the continuous flow tubular reactor with a residence time of 59 s and under a reaction pressure of 400 kPa. After the phase-separation of the obtained reaction mixture, and organic phase was washed by water, and subjected to vacuum distillation (5 kPa, 75° C.) and filtration, to give a light yellow and transparent liquid; wherein the yield was 90%. The obtained product is methylene bis-(di-ethylamino-dithioformate) and has a kinematic viscosity of 15.0 cSt, a nitrogen content of 7.6 and the ASTM colour of the product is 1.0.

Example 6

A heating-cooling circulator was used to heat and cool a continuous flow tubular reactor, and the temperature of the continuous flow tubular reactor was set at 70° C. After the temperature became stable, raw material A: a mixture fluid of 300 ml di-isobutylamine and 200 ml 30% aqueous solution of sodium hydroxide was fed through a constant-flow pump into the continuous flow tubular reactor with a flow rate of 50 ml/min; meanwhile, raw material B: a mixed solution of 115 ml carbon disulfide and 65 ml dichloromethane was fed through a constant-flow pump into the continuous flow tubular reactor with a flow rate of 18 ml/min. The channel diameter of the reactor was 50 μm. Said raw materials were reacted in the continuous flow tubular reactor with a residence time of 57 s and under a reaction pressure of 800 kPa. After the phase separation of the obtained reaction mixture, organic phase was washed with water, and subjected to vacuum distillation (5 kPa, 80° C.) and filtration, to give a light yellow and transparent liquid; wherein the yield was 90%. The obtained product is methylene bis-(di-isobutylamino-dithioformate) and has a kinematic viscosity of 15.1 cSt, a nitrogen content of 6.7 and the ASTM colour of the product is 1.0.

Example 7

A heating-cooling circulator was used to heat and cool a continuous flow tubular reactor, and the temperature of the continuous flow tubular reactor was set at 55° C. After the temperature became stable, raw material A: a mixture fluid of 178 ml diethylamine and 200 ml 30% aqueous solution of sodium hydroxide was fed through a constant-flow pump into the continuous flow tubular reactor with a flow rate of 45 ml/min; meanwhile, raw material B: a mixture fluid of 115 ml carbon disulfide and 60 ml dichloromethane, was fed through a constant-flow pump into the continuous flow tubular reactor with a flow rate of 20 ml/min. The channel diameter of the reactor was 200 μm. Said raw materials were reacted in the continuous flow tubular reactor with a residence time of 59 s and under a reaction pressure of 500 kPa. After the phase separation of the obtained reaction mixture, organic phase was washed with water, and subjected to vacuum distillation (5 kPa, 75° C.) and filtration, to give a light yellow and transparent liquid; wherein the yield was 88%. The obtained product is methylene bis-(diethylamino-dithioformate) and has a kinematic viscosity of 15.1 cSt, a nitrogen content of 7.5 and the ASTM colour of the product is 1.0.

Example 8

A heating-cooling circulator was used to heat and cool a continuous flow tubular reactor, and the temperature of the continuous flow tubular reactor was set at 60° C. After the temperature became stable, raw material A: a mixture fluid of 178 ml diethylamine and 200 ml 30% aqueous solution of sodium hydroxide was fed through a constant-flow pump into the continuous flow tubular reactor with a flow rate of 50 ml/min; meanwhile, raw material B: a mixed solution of 115 ml carbon disulfide and 60 ml dichloromethane was fed through a constant-flow pump into the continuous flow tubular reactor with a flow rate of 23 ml/min. The channel diameter of the reactor was 100 μm. Said raw materials were reacted in the continuous flow tubular reactor with a residence time of 53 s and under a reaction pressure of 700 kPa. After the phase separation of the obtained reaction mixture, organic phase was washed with water, and subjected to vacuum distillation (5 kPa, 75° C.) and filtration, to give a light yellow and transparent liquid; wherein the yield was 89%. The obtained product is methylene bis-(di-ethylamino-dithioformate) and has a kinematic viscosity of 15.0 cSt, a nitrogen content of 7.6 and the ASTM colour of the product is 1.1.

Comparative Example 9

A heating-cooling circulator was used to heat and cool a continuous flow tubular reactor, and the temperature of the reactor was set at 60° C. After the temperature became stable, raw material A: a mixture fluid of 300 ml di-n-butylamine and 200 ml 30% aqueous solution of sodium hydroxide was fed through a constant-flow pump into the reactor, and the flow rate is kept at 50 ml/min; meanwhile, raw material B: a mixture fluid of 110 ml carbon disulfide and 60 ml dichloromethane was fed through a constant-flow pump into the continuous flow tubular reactor, and the flow rate was kept at 20 ml/min. The channel diameter of the reactor was 3500 μm. Said raw materials were reacted in the continuous flow tubular reactor with a residence time of 55 s and under a reaction pressure of 300 kPa. After the phase separation of the obtained reaction mixture, organic phase was washed with water, and subjected to vacuum distillation (5 kPa, 70° C.) and filtration, to give a light yellow and transparent liquid; wherein the yield was 68%. The obtained product is methylene bis-(di-n-butylamino-dithioformate) and has a kinematic viscosity of 15.4 cSt, a nitrogen content of 6.9 and the ASTM colour of the product is 2.0.

What is claimed is:

1. A process for preparing methylene bis-(dialkylamino-dithioformate) in one step, wherein the process comprises supplying dialkylamine, sodium hydroxide, dichloromethane and carbon disulfide as raw materials into a continuous flow tubular reactor with a channel diameter of 0.1 μm to 3 mm to perform a reaction in one step under a reaction temperature controlled to be 10 to 100° C.

2. The process according to claim 1, wherein said continuous flow tubular reactor comprises one reaction plate or a plurality of reaction plates connected in series, and said reaction plate consists of two heat transfer layers and one reaction layer, the middle layer being the reaction layer.

3. The process according to claim 2, wherein the reaction spaces in said reaction layer are a plurality of spaces in a shape of heart or similar to heart formed by channels, the spaces being connected in series by the channels having a diameter of 0.1 μm to 3 mm.

4. The process according to claim 2, wherein said continuous flow tubular reactor comprises 2 to 8 reaction plates.

5. The process according to claim 2, wherein a temperature required for the reaction is controlled by a heat conducting fluid in the heat transfer layers of the reaction plate, said heat conducting fluid being one of water, saturated steam, mineral oil or diphenyl mixture.

6. The process according to claim 1, wherein a reaction pressure is 100 to 1800 kPa.

7. The process according to claim 1, wherein a molar ratio of dialkylamine to carbon disulfide is 1:1 to 1:1.7, a molar ratio of dialkylamine to sodium hydroxide is 1:1 to 1:1.6, and a molar ratio of dialkylamine to dichloromethane is 1:0.5 to 1:0.9.

8. The process according to claim 7, wherein the molar ratio of dialkylamine to carbon disulfide is 1:1 to 1:1.4, the molar ratio of dialkylamine to sodium hydroxide is 1:1 to 1:1.3, and the molar ratio of dialkylamine to dichloromethane is 1:0.5 to 1:0.8.

9. The process according to claim 1, wherein a residence time of the reaction is 10 to 100 s.

10. The process according to claim 1, wherein in said continuous flow tubular reactor, a reaction temperature is 40 to 90° C., a residence time is 24 to 96 s, and a reaction pressure is 200 to 1800 kPa.

11. The process according to claim 1, wherein a temperature difference, a residence time and the channel diameter of said continuous flow tubular reactor conform to the following relation formula:

$$\Delta T = k \times \frac{d}{4tU}$$

in the above formula:
ΔT represents a numerical value of the temperature difference between an inside and an outside of the reaction plate measured in K, wherein ΔT<2;
U represents a numerical value of a heat transfer coefficient of the reaction plate measured in W/μm²·K, which depends on the materials used;
d represents a numerical value of the channel diameter of the reaction plate measured in μm;
t represents a numerical value of the residence time measured in s;
k represents an empirical coefficient, wherein $1.87 \times 10^{-9} \leq k \leq 3.74 \times 10^{-10}$.

12. The process according to claim 1, wherein the process further comprises a vacuum distillation step of the obtained reaction products to give methylene bis-(dialkylamino-dithioformate).

13. The process according to claim 12, wherein a distillation pressure of said vacuum distillation is 5 kPa, and a distillation temperature is 40 to 100° C.

14. The process according to claim 1, wherein said sodium hydroxide is an aqueous solution with a mass concentration of 13 to 50%.

15. The process according to claim 1, wherein the continuous flow tubular reactor has a channel diameter of 10 μm to 1000 μm.

16. The process according to claim 1, wherein the continuous flow tubular reactor has a channel diameter of 20 μm to 200 μm.

17. The process according to claim 3, wherein the spaces are connected in series by the channels having a diameter of 10 μm to 1000 μm.

18. The process according to claim 3, wherein the spaces are connected in series by the channels having a diameter of 20 μm to 200 μm.

* * * * *